United States Patent [19]
Ade et al.

[11] Patent Number: 5,853,665
[45] Date of Patent: Dec. 29, 1998

[54] APPARATUS AND METHOD FOR MONITORING VENT LINE VACUUM

[75] Inventors: Rodrigue Ade, Miami; Robert Autrey, Pembroke Pines; Santiago Galvez; Pedro E. Leon, both of Miami; Michael A. Krou, Davie, all of Fla.

[73] Assignee: Coulter International Corp., Miami, Fla.

[21] Appl. No.: 931,178

[22] Filed: Sep. 16, 1997

[51] Int. Cl.⁶ .................................................. G01N 1/14
[52] U.S. Cl. .............................. 422/62; 422/67; 422/100; 422/112; 436/55; 436/180
[58] Field of Search .............................. 422/62, 67, 100, 422/112; 436/54, 55, 180

[56] References Cited

U.S. PATENT DOCUMENTS

| | | |
|---|---|---|
| 3,876,374 | 4/1975 | Burns . |
| 4,387,076 | 6/1983 | Cabrera et al. . |
| 4,609,017 | 9/1986 | Coulter et al. . |
| 5,094,961 | 3/1992 | Del Valle et al. ...................... 436/180 |
| 5,158,751 | 10/1992 | del Valle et al. . |
| 5,279,796 | 1/1994 | Parker et al. . |
| 5,665,601 | 9/1997 | Kilmer ...................................... 436/54 |

*Primary Examiner*—Jeffrey Snay
*Attorney, Agent, or Firm*—Warren W. Kurz

[57] ABSTRACT

An apparatus for automatically drawing a blood sample from a sealed container having an internal pressure below that of atmospheric pressure comprises an aspirating needle which serves to pierce the sealed container to aspirate liquid from the container, and to vent the interior of the container to the surrounding atmosphere through a suitable vent line connected to the needle. Such apparatus further comprises a vacuum pump connected to the needle through an aspiration line for aspirating blood from the sealed container. To warn the user of the possibility that fluid (e.g. cleansing diluent) in the aspirating needle has been drawn into the sealed container in the event of a vent line failure, apparatus is provided for detecting the pressure in the container immediately after the aspirating needle has pierced the container seal, and for comparing this pressure with a predetermined nominal value (typically, the negative pressure rating of the vacuum pump).

10 Claims, 4 Drawing Sheets

APPARATUS AND METHOD FOR MONITORING VENT LINE VACUUM

BACKGROUND OF THE INVENTION

1. Field of the Invention

This invention relates to the field of fluid handling, and more particularly it relates to improvements in apparatus for detecting failure of a venting system commonly used in blood-analyzing apparatus for depleting residual negative pressure in a sealed container.

2. Discussion of the Prior Art

In certain fully-automated blood analyzing instruments, such as the ONYX blood analyzer manufactured by Coulter Corporation, Miami, Florida, there is provided an automated apparatus for aspirating a precise volume of blood sample from a container. As taught by the commonly assigned U.S. Pat. No. 4,609,017, such container is typically a sealed test tube which is handled by automatic or semi-automatic feed mechanisms that operate to position the sample-containing tube so that its contents can be extracted or aspirated by the instrument. Aspiration of a blood sample from the sealed tube is typically accomplished by an aspirating needle which pierces a tube-sealing membrane and, in conjunction with a pump connected thereto, extracts the blood sample. The extracted blood sample is then transmitted through a fluid conduit line to a metering valve assembly, e.g. of the type taught by the commonly assigned U.S. Pat. No. 5,158,751 from where it will be delivered to a testing station provided within the instrument for analysis. After the aspirated sample passes to the testing station, the fluid conduit line and the metering valve assembly are flushed with diluent solution in order to wash and prepare the apparatus for the next sample. The aspirating needle is typically washed in the manner disclosed in the commonly assigned U.S. Pat. No. 5,279,796.

Normally, the sealed blood-containing containers used in blood analyzing instruments of the type described above are evacuated to a predetermined negative pressure prior to receiving a blood sample. Thus, when the container seal is punctured, by a needle connected to a blood supply, blood is drawn into the container by the negative pressure therein. Often, a residual negative pressure remains in the container after the blood supply is disconnected, i.e., after the seal-puncturing needle has been removed. This residual negative pressure in the specimen-containing container can give rise to contamination or blood dilution problems if care is not taken to relieve or vent the residual negative pressure prior to aspirating the sample into the blood analyzing instrument. Should a negative pressure be allowed to remain in the container when the blood aspirating needle of the analyzer punctures the container seal for the purpose of aspirating the sample, any fluid in the aspirating needle or a fluid conduit line connected thereto will be sucked into the container, and thereby contaminate or dilute the sample. Since it is common to cleanse the aspirating needle and its associated plumbing with a liquid diluent between successive blood samplings, any residual diluent in the needle and its associated blood lines will thus contaminate the sample if venting of the residual negative pressure is not attended to.

To overcome the above-noted problem (sometimes referred to in the industry as the "reverse flow" problem), many instruments provide a means for venting the residual negative pressure inside a container to atmospheric pressure prior to aspiration of the sample. For example, some instruments are designed to repeatedly pierce the container seal with the aspiration needle. However, this approach is undesirable in that it can cause premature deterioration of the container seal. A preferred method of ventilation makes use of a ventilation line connected to the aspirating needle that allows the negative pressure inside the container to equilibrate with the ambient pressure immediately after penetration of the container seal by the needle.

In some automatic blood analyzing devices, the aspiration needle contains two completely isolated, side-by-side chambers. Such a needle is disclosed in the commonly assigned U.S. Pat. No. 4,387,076. One chamber is used for aspiration purposes and is connected to a pump via a fluid conduit line. It is through this chamber that sample blood is sucked into the instrument for analysis. Also, upon complete aspiration of a sample, this chamber is flushed with diluent solution so as to prepare for aspiration of the next sample. The other chamber is connected to a vent line which commonly splits into two individual lines, each of which connects to ambient air through a check valve. The check valves function as gates that open and close depending on the comparative negative pressures of the container and atmosphere. For example, if the negative pressure of the container is less than that of atmosphere, the check valve will open and allow for ventilation of the container. However, if the negative pressure of the container is greater than that of atmosphere, the check valve will remain closed since there is no need to ventilate the container. The purpose of splitting the vent line is to provide a back-up should one line become obstructed or any valve malfunction.

A problem noted with the line approach described above concerns the situation where the vent line is obstructed at a point prior to the line splitting into two individual lines, or in the event both check valves malfunction. Normally, this is not a problem if the obstruction or malfunction occurs to only one of the vent lines or check valves, since ventilation can properly take place through the other line. However, if both vent lines are obstructed or both check valves malfunction, then there is no way for the residual negative pressure within the container to ventilate.

As mentioned above, a failure of the ventilation means can lead to contamination of the blood sample if the negative pressure inside the container is greater than that of the source used for aspiration. Thus, it would be desirable to provide in a blood-analyzing instrument, apparatus for detecting a failure of the ventilation means, so that the instrument can be either disabled or the operator warned of the possibility that residual diluent has entered the container and contaminated the blood sample.

SUMMARY OF THE INVENTION

In view of the foregoing, an object of the present invention is to provide an apparatus for detecting a failure of a venting mechanism of the type described so that the possibility of dilution or contamination of the sample may be detected.

Like the prior art, the blood analyzer of the invention comprises: an apparatus for automatically drawing a blood sample from a sealed container having an internal pressure below atmospheric pressure. Such apparatus comprises an aspirating needle for both piercing the seal to aspirate blood from the container, and venting the interior of the container to the surrounding atmosphere through venting means operatively connected to the needle. Such apparatus further comprises a vacuum pump for aspirating the liquid from the container. The vacuum pump is connected to the aspirating needle through an aspirating line. In contrast with the prior art analyzers however, the blood analyzer of the invention features means for sensing a failure of the venting means which comprise: (i) means for producing a first signal indicative of the negative pressure associated with the vacuum pump; (ii) means for producing a second signal indicative of the internal pressure within the sealed container; and (iii) logic and control means for storing a predetermined nominal value, for comparing the first and second signals to the predetermined nominal value, and producing a third signal in the event that either the internal pressure is less than the predetermined nominal value or the negative pressure is other than the predetermined nominal value. Preferably, the means for producing the first and second signal comprises a pressure-sensitive transducer, such transducer being connected to the aspirating line through a check valve and to the system vacuum pump line through a valve controlled by the logic and control means.

As will be better appreciated from the ensuing Detailed Description of Preferred Embodiments, the invention is particularly advantageous vis-a-vis the prior art discussed above in that, in the event of a ventilation failure (i.e., vent line obstruction or valve malfunction), sample aspiration can be interrupted and the operator warned of the possibility of blood sample contamination. This alerts the operator to the possibility of erroneous results, and allows him or her to take the appropriate remedial steps.

The invention will be better understood from the ensuing description of preferred embodiments, reference being made to the accompanying drawings.

DETAILED DESCRIPTION OF PREFERRED EMBODIMENTS

Figure 1:
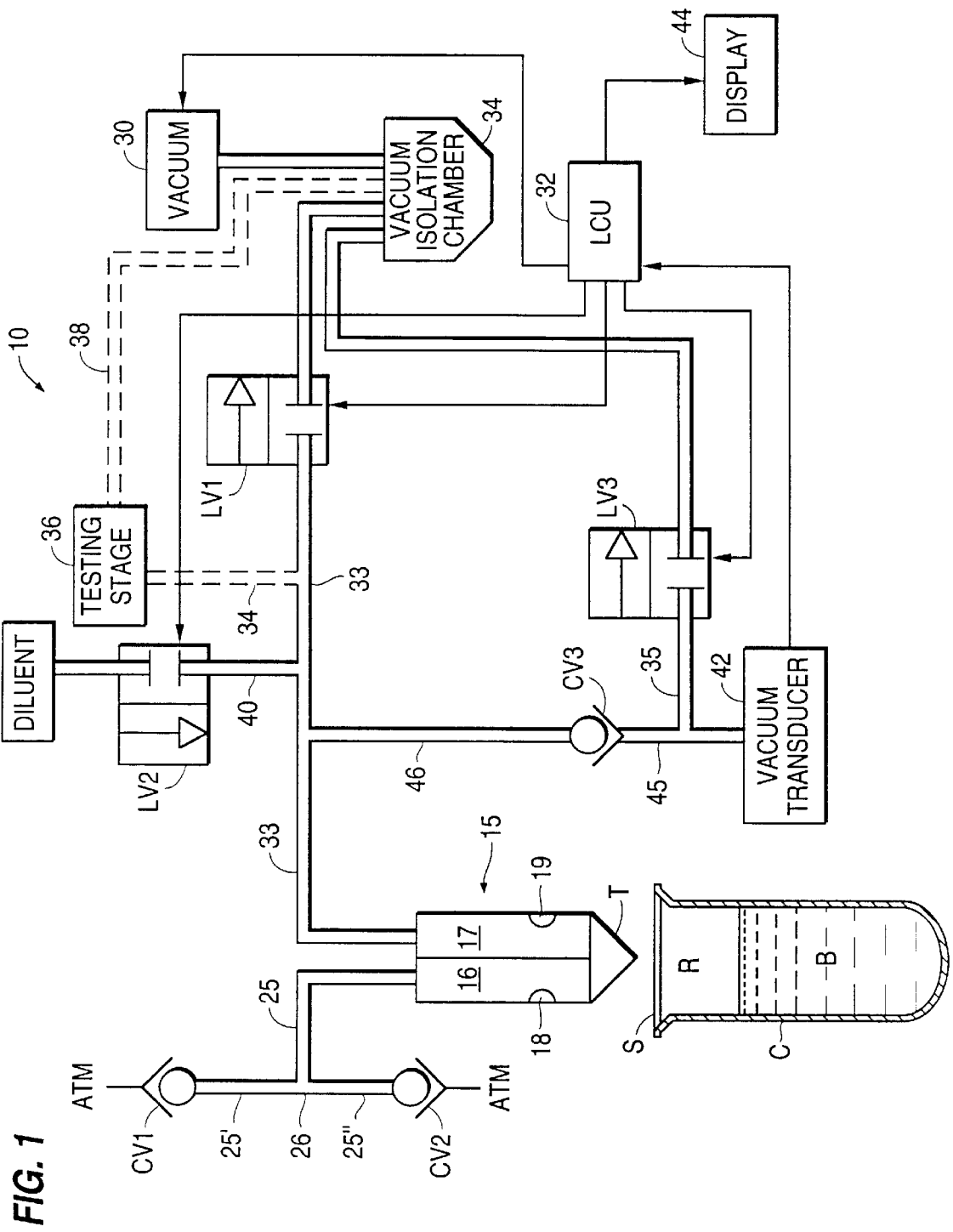
FIG. 1 is a schematic illustration of a blood-analyzing apparatus using a preferred embodiment of the invention.

Referring now to the drawings, FIG. 1 schematically illustrates the basic components of a blood analyzing apparatus 10 embodying the present invention. Such apparatus is generally adapted to aspirate a predetermined volume of blood B from a blood sample container C and, in a known manner, to analyze such blood in a testing stage 36, e.g., to enumerate various different types of blood cells in the sample. As shown, container C is capped by a thin, pliable seal S, such as a rubber cap, which can be punctured by an aspiration needle 15 (enlarged for clarity purposes) through which all or a desired portion of the blood sample can be extracted from the container. Prior to aspiration, it is not uncommon for the container's spatial region R, located between seal S and the upper surface of the blood sample B, to exhibit a negative pressure (i.e., less than atmospheric pressure). This negative pressure is the residue of a somewhat lower negative pressure used during the blood collection process to draw blood into the container from a blood source, typically a patient's vein. Ideally, the residual negative pressure in region R should be vented to atmosphere as soon as the aspirating needle punctures the container's seal; otherwise, this negative pressure, should it exceed the negative pressure force applied to the aspirating needle by pump 30, will draw any liquid present in the needle and its associated conduit into the container and thereby contaminate or undesirably dilute the sample. This is the "reverse flow" problem noted above.

To achieve the above-noted venting process, it is known to use a dual chamber aspirating needle of the type shown in FIG. 1. Specifically, needle 15 comprises a pair of parallel internal chambers 16 and 17, one chamber 16 serving to vent the residual negative pressure in container region R to atmosphere, and the other chamber 17 serving to aspirate blood for analysis. Needle apertures 18 and 19 located in the vicinity of the needle tip T provide a means for introducing air and blood into chambers 16 and 17 for venting and aspirating purposes. Connected to the venting chamber 16 is a vent line 25 which divides into two vent lines 25' and 25" at a "T" junction 26. Vent lines 25' and 25" communicate with atmospheric pressure ATM (i.e., ambient air) via conventional check valves CV1 and CV2, respectively. Thus, as the aspirating needle punctures the container seal, any residual negative pressure in region R will normally be vented to atmosphere through either or both of the check valves in vent line 25' and 25".

Once residual negative pressure is properly vented, aspiration of a blood sample from container C is effected by a computer-controlled aspiration pump 30 which operates under the control of a logic and control unit (LCU) 32. Pump 30 is operatively connected to the needle chamber 17 of the aspirating needle and applies a predetermined negative pressure thereto through a vacuum isolation chamber 34 and an aspiration line 33. A solenoid-operated valve LV1, operating under the control of LCU 32, controls the application of negative pressure to the aspirating needle. Once aspirated, the sample blood enters the testing stage 36 through line 37 for analysis; upon completion of testing, the analyzed sample enters vacuum isolation chamber 34 through line 38 from where it will be disposed. Thus, chamber 34 serves two purposes: (1) connecting pump 30 to aspiration line 33 and needle 15, and (2) acting as a collection reservoir for analyzed blood samples prior to disposal. After aspiration of a sample is complete, diluent solution (i.e. backwash solution) is selectively applied to the aspiration line through a solenoid-controlled valve LV2 located in a diluent supply line 40. The flushing of diluent solution cleanses and prepares the aspiration line and needle for aspiration of subsequent blood samples. Preferably, the opening and closing of valves LV1, LV2 and LV3 is controlled by a computer program under which LCU 32 operates. One skilled in the art may appreciate that although valves LV1, LV2 and LV3 are schematically disclosed in their closed (i.e., no fluid flow) position, they may opened when so required by the invention.

Now, in accordance with the present invention, a method and apparatus are provided for detecting a condition in which the negative pressure within the container is less than the negative pressure associated with pump 30, as may be the case in which the venting system has failed. Under such condition, diluent in the aspiration line can be sucked into the sample container and undesirably dilute or otherwise contaminate the sample. As noted, the venting system described heretofore has a certain amount of redundancy in that the vent line 25 is split in two to provide two venting outlets. Nevertheless, should an obstruction appear in line 25 before the split, or should both check valves fail to operate, the "reverse flow" problem can still occur. To warn an operator of the possible occurrence of the problem, the method of the invention basically comprises the steps of: (a) producing a first signal indicative of the negative pressure applied by vacuum pump 30; (b) comparing the first signal to a predetermined nominal value stored within LCU 32; (c) producing a second signal indicative of the internal pressure within container C; (d) comparing the second signal with a predetermined nominal negative pressure value stored within LCU 32; and (e) producing a third (warning) signal in the event that either said internal pressure is less than said predetermined nominal value, or said negative pressure is other than the predetermined nominal value. Alternatively, it may be appreciated by one skilled in the art that the inventive method may comprise the steps of: (a) producing a first signal indicative of the negative pressure applied by vacuum pump 30; (b) producing a second signal indicative of the negative pressure within container C; (c) comparing the two signals; and (d) producing a third (warning) signal in the event the comparison of signals indicates that the container negative pressure is less than the pump negative pressure. Preferably, in either of the two alternative methods, the third signal may be used to disable the aspirator until another sample container is presented for aspiration.

To carry out the above method, apparatus is provided for detecting both the negative pressure applied by the pump and the negative pressure within the sample container prior to aspiration. To detect the negative pressure of pump 30, transducer 42 is connected to vacuum isolation chamber 34 through valve LV3. As for the negative pressure within the sealed container, it is sensed by the connection of transducer 42 to aspiration line 33 through lines 45 and 46 and check valve CV3. Below is a detailed description of how the method of the invention is carried out by the respective parts of the apparatus.

Prior to each aspiration, solenoid valves LV1, LV2 are closed so that the negative pressure associated with vacuum pump 30 may be determined. As was mentioned above, this is done by the connection of vacuum transducer 42 to the pump 30 through vacuum isolation chamber 34, vacuum line 35 and opened check valve LV3. In particular, vacuum transducer 42 senses the negative pressure inside vacuum isolation chamber 34, which is equivalent to the negative pressure of pump 30, and produces a corresponding first electrical signal indicative of the level therein. This first electrical signal is transmitted to the LCU 32 which will in turn compare it to a predetermined nominal negative pressure value stored therein (typically, the predetermined nominal negative pressure value stored within LCU 32 is equal to the pressure rating of pump 30). In the event the transducer output indicates the pump negative pressure is other than "nominal," the aspiration process may be interrupted by an electrical signal produced by LCU 32, and the operator notified on display 44; otherwise, if the negative pressure associated with pump 30 is equal to the predetermined nominal negative pressure stored within LCU 32, check valve LV3 will close and the apparatus will proceed to pierce the seal of the container. One skilled in the art will appreciate that when LV3 closes, the negative pressure in lines 35 and 45 will be equal to that of vacuum pump 30. Preferably, CV3 is located a far enough distance from the junction between line 33 and line 46 to prevent the build-up of diluent solution crystallization on the valve.

Immediately after piercing, valves LV1, LV2 and LV3 remain closed in order to allow an accurate sensing of the negative pressure inside the sealed container by vacuum transducer 42. If the negative pressure inside the sealed container is less than the negative pressure associated with pump 30, i.e. the negative pressure now present in line 45, check valve CV3 will open and transducer 42 will sense a corresponding drop in the negative pressure of line 45. In response, transducer 42 will produce a second electrical signal indicative of the new negative pressure present in line 45, i.e. the negative pressure inside the sealed container, and transmit said second signal to LCU 32. In turn, LCU 32 will compare the second electrical signal to the predetermined nominal negative pressure value stored therein. If the comparison indicates that the negative pressure inside the sealed container is less than the predetermined nominal negative pressure value, LCU 32 may produce a third signal which will cease operation and/or warn the operator on display 44 of the possibility of blood sample contamination. However, if the negative pressure inside the container is not less than the predetermined nominal negative pressure value stored within LCU 32, then there is no possibility of diluent being drawn into the container and the instrument may proceed to aspirate the blood sample. In this case, transducer 42 will not directly sense the negative pressure inside the sealed container; rather, transducer 42 will actually produce an electrical signal indicative of the negative pressure in line 45. Because the negative pressure in line 45 has not changed, LCU 32 will determine that the negative pressure inside the sealed container is not less than the predetermined nominal negative pressure value, thereby indicating that sample dilution has not occurred. It is preferred that CV3 not be located too close to the vacuum transducer 42 so as to reduce the amount of air in line 46 that would have to be evacuated in order for CV3 to open.

The above-described apparatus is based on the programming of a predetermined "nominal" negative pressure value (i.e., the rating of the vacuum pump) within LCU 32. However, it may be appreciated by one skilled in the art that, alternatively, the nominal value may be first sensed by transducer 42 and then stored in LCU 32. That is, prior to piercing the sealed container transducer 42 senses the negative pressure in vacuum isolation chamber 34 and stores this negative pressure value in LCU 32. This alternative method allows for the use of vacuum pumps having various vacuum ratings without the need to alter the programming of LCU 32.

Figure 3:
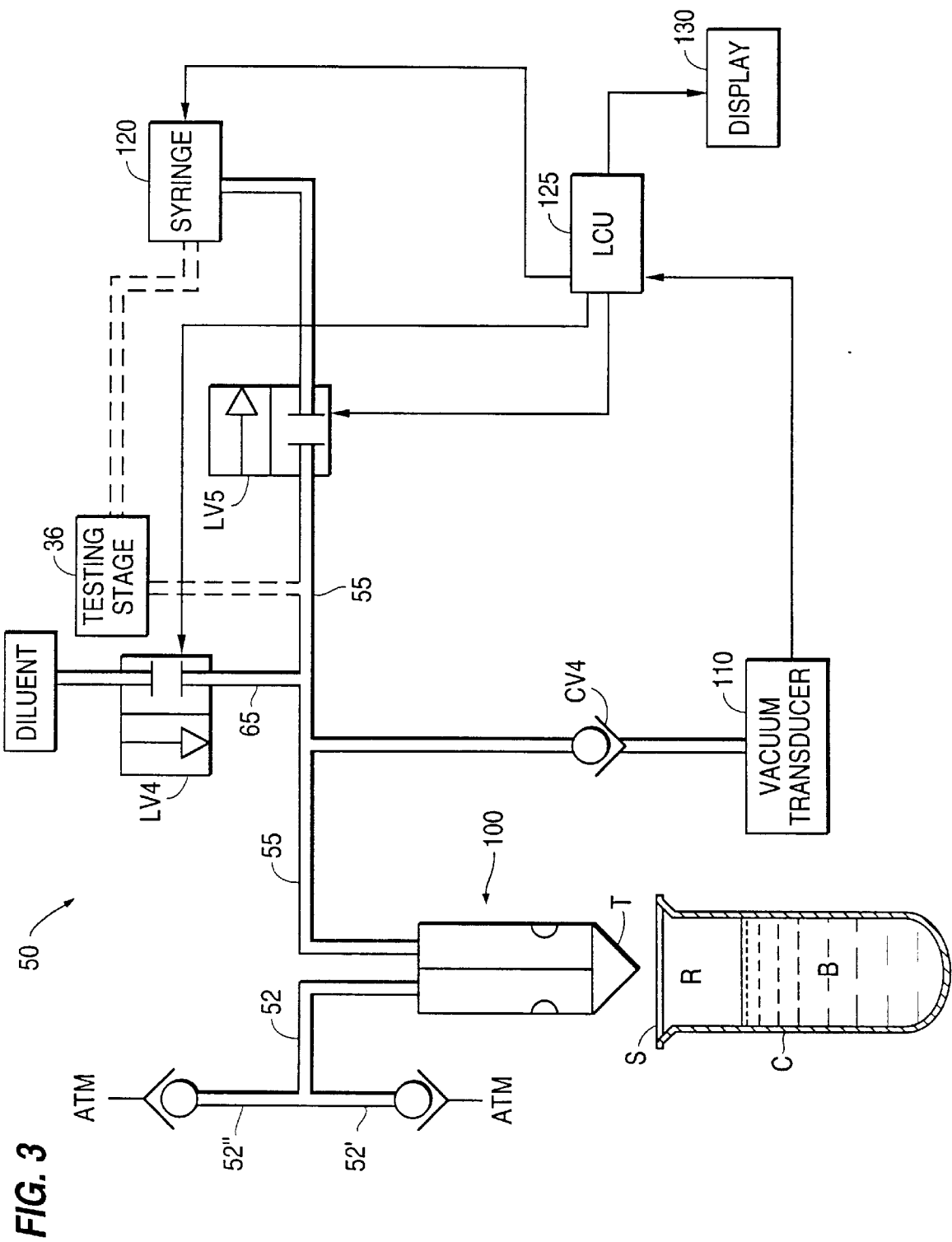
FIG. 3 is a schematic illustration of a blood-analyzing apparatus using an alternative embodiment of the invention.

FIG. 3 displays an alternative embodiment of the invention. Specifically, the layout disclosed in FIG. 3 is for use with blood-analyzers which utilize a negative pressure source other than a vacuum pump (e.g., syringe) as an aspiration source. Like the layout in FIG. 1, FIG. 3 contains an aspirating needle 100, check valve CV4, solenoid valves LV4 and LV5, vacuum transducer 110, aspiration line 55, backwash line 65, and vent line 52 which splits into individual lines 52' and 52". Operationally, the layout in FIG. 3 functions like that of FIG. 1 except that vacuum transducer 110 does not sense the negative pressure of pump 120 prior to piercing of the sealed tube. Rather, the vacuum transducer 110 is set up to detect the negative pressure inside of the container should valve CV4 open up. As in FIG. 1, should the negative pressure in the container exceed that of the predetermined system negative pressure, control system 125 will cease aspiration and the operator is warned by display 130.

Figure 2:
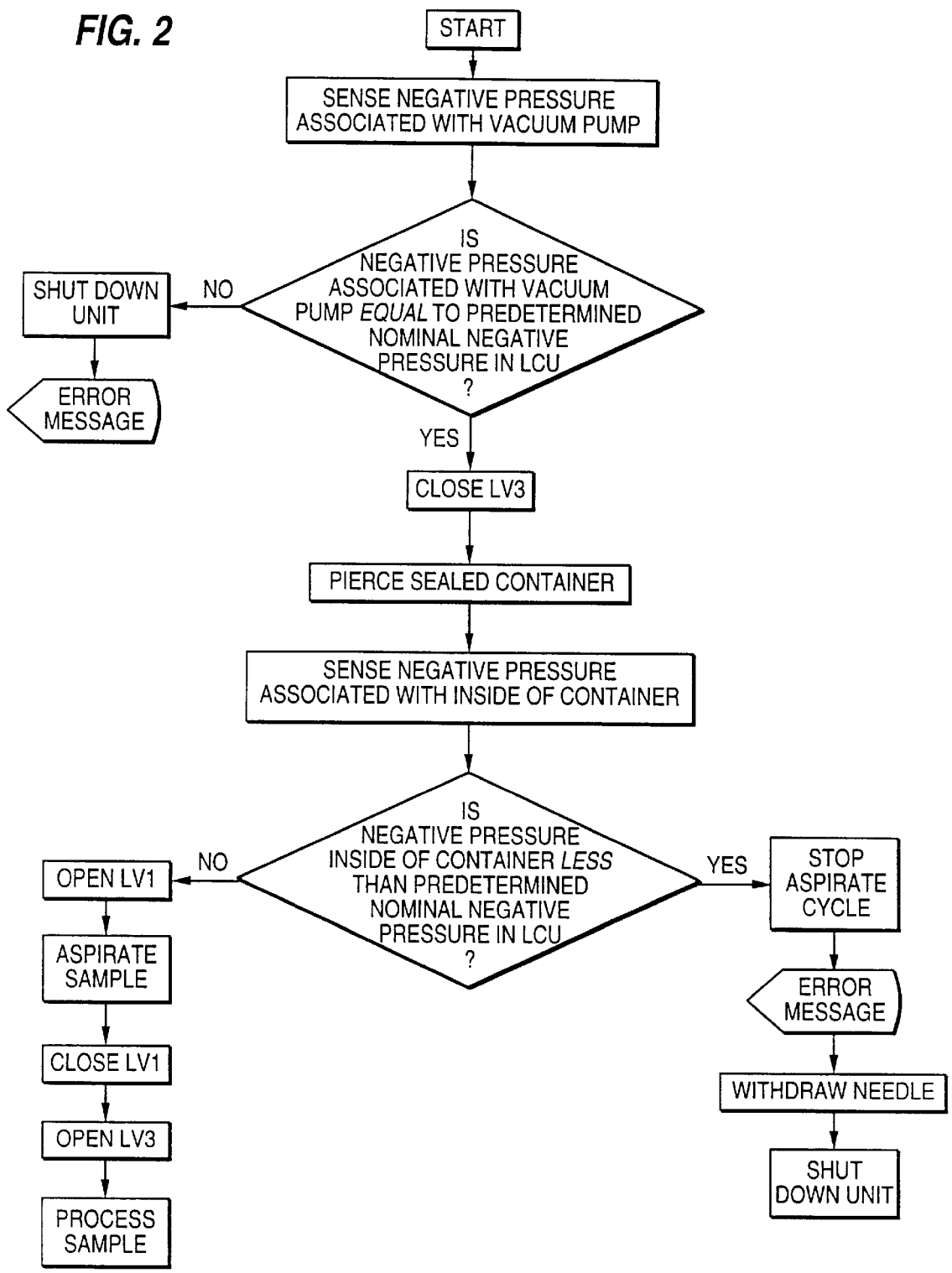
FIG. 2 is a flowchart of the sequence of operation carried out by the logic and control unit of the FIG. 1 apparatus.
Figure 4:
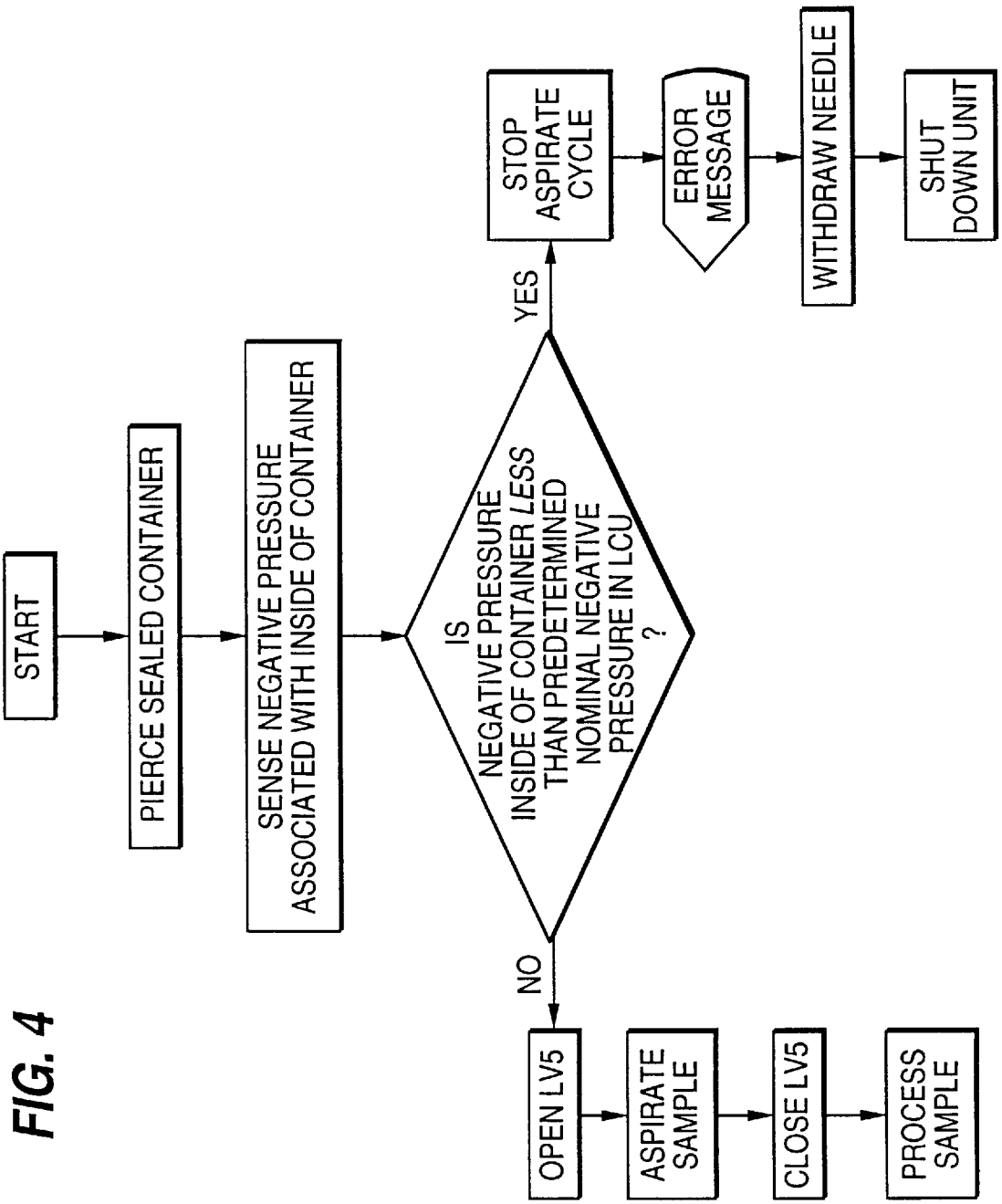
FIG. 4 is a flowchart of the sequence of operation carried out by the logic and control unit of the FIG. 3 apparatus.

FIGS. 2 and 4 disclose flowsheets respectively indicating the program carried out by the LCU in vacuum pump systems and syringe systems having predetermined nominal negative pressure amount. Referring to FIG. 2, the LCU is programmed as follows: first, the negative pressure of the vacuum pump 30 is sensed. In the event this pressure does not equal a predetermined nominal value stored in the LCU memory (e.g. a read-only memory ROM) the aspirating apparatus is shut down so that the pump pressure can be appropriately adjusted or corrected. If the pump pressure is nominal, then the LCU operates to close valve LV3 and move needle 15 in a downward direction to pierce seal S. The LCU then determines from the output of transducer 42, whether the pressure inside the container is greater than, or less than the predetermined nominal pressure stored in the LCU. If it is greater, then the LCU: operates to (1) open valve LV1; (2) aspirate a sample; (3) close LV1; (4) open LV3; and (5) process the sample. If the pressure in the container is less than the nominal pressure, then the LCU operates to: (1) stop the aspiration cycle; (2) display an error message on display 44; (3) withdraw needle 15; and (4) shut down unit. At this point, the operator will then be aware of the possibility that sample contamination or dilution has occurred.

In FIG. 4, the LCU is programmed as follows: first, needle 100 is moved downward to pierce seal S. The LCU 125 then determines, from the output of transducer 110, whether the pressure inside the container is greater than, or less than the predetermined nominal pressure stored in the LCU. If it is greater, then the LCU operates to: (1) open LV5; (2) aspirate sample; (3) close LV5; and (4) process sample. If it is less, then the LCU operates to: (10) stop aspiration cycle; (2) display error message on display 130; (4) withdraw needle 100; and (5) shut down unit.

The invention has been described with reference to certain preferred embodiments but it will be appreciated that variations and modifications can be effected without departing from the spirit of the invention. Such variations and modifications are intended to fall within the scope of the appended claims.

What is claimed is:

1. In an apparatus for automatically drawing a blood sample from a sealed container having an internal pressure below atmospheric pressure, said container being sealed by a pierceable cap, said apparatus comprising: (a) an aspirating needle for both piercing said cap to aspirate blood from said container, and venting the interior of the container to the surrounding atmosphere through venting means operatively connected to said aspirating needle; and (b) a vacuum pump for aspirating the blood from the container, said vacuum pump being connected to said aspirating needle through an aspiration line, the improvement comprising:

means for sensing a failure of the venting means, said failure-sensing means comprising: (i) means for producing a first signal indicative of the negative pressure associated with said vacuum pump; (ii) means for producing a second signal indicative of said internal pressure within said sealed container after said cap has been pierced by said aspirating needle; and (iii) logic and control means for storing a predetermined nominal value and for comparing said first and second signals to said predetermined nominal value, said logic and control means further producing a third signal in the event that either said internal pressure is less than said predetermined nominal value or said negative pressure is other than said predetermined nominal value.

2. The apparatus of claim 1 wherein said venting means comprises a vent line connected to said aspirating needle.

3. The apparatus of claim 1 wherein said means for producing said first and second signals comprises a vacuum transducer connected to said aspiration line through a check valve, and to said vacuum pump through a valve controlled by said logic and control means.

4. In an apparatus for automatically drawing a blood sample from a sealed container having an internal pressure below atmospheric pressure, said container being sealed by a pierceable cap, said apparatus comprising: (a) an aspirating needle for both piercing said cap to aspirate blood from said container, and venting the interior of the container to the surrounding atmosphere through venting means operatively connected to said aspirating needle; and (b) a vacuum pump for aspirating the blood from the container, said vacuum pump being connected to said aspirating needle through an aspiration line, the improvement comprising:

means for sensing a failure of the venting means, said failure-sensing means comprising: (i) means for producing a first signal indicative of the negative pressure associated with said vacuum pump; (ii) means for producing a second signal indicative of said internal pressure within said sealed container after said cap has been pierced by said aspirating needle; and (iii) logic and control means for comparing said first and second signals and producing a third signal in the event the comparison of said first and second signals indicates said internal pressure is less than said negative pressure.

5. The apparatus of claim 4 wherein said venting means comprises a vent line connected to said aspirating needle.

6. The apparatus of claim 4 wherein said means for producing said first and second signals comprises a vacuum transducer connected to said aspiration line through a check valve, and to said vacuum pump through a valve controlled by said logic and control means.

7. In an apparatus for automatically drawing a blood sample from a sealed container having an internal pressure below atmospheric pressure, said container being sealed by a pierceable cap, said apparatus comprising: (a) an aspirating needle for both piercing said cap to aspirate blood from said container, and venting the interior of the container to the surrounding atmosphere through venting means operatively connected to said aspirating needle; and (b) a syringe for aspirating the blood from the container, said syringe being connected to said aspirating needle through an aspiration line, the improvement comprising:

means for sensing a failure of the venting means, said failure-sensing means comprising: (i) means for producing a first signal indicative of said internal pressure within said sealed container after said cap has been pierced by said aspirating needle; and (ii) logic and control means for: (a) storing a predetermined nominal value; (b) comparing said first signal and said predetermined nominal value; and (c) producing a third signal in the event the comparison of said first signal and said predetermined nominal value indicates said internal pressure is less than said predetermined nominal value.

8. The apparatus of claim 7 wherein said venting means comprises a vent line connected to said aspirating needle.

9. The apparatus of claim 7 wherein said means for producing said first signal comprises a vacuum transducer connected to said aspiration line through a check valve.

10. In a method for aspirating a liquid from a sealed container having an internal pressure that may be less than a nominal vacuum pressure applied to a needle used to aspirate such liquid from the container, the improvement comprising a method for detecting and signaling such condition, said method comprising the steps of:

(a) producing a first signal indicative of the nominal vacuum pressure;

(b) producing a second signal indicative of the vacuum pressure within the sealed container;

(c) comparing said first and second signals; and (d) producing a third signal in the event the comparison of said first and second signals indicates that the container vacuum pressure is less than that of said nominal vacuum pressure.

* * * * *